United States Patent
Shikaumi (10) Patent No.: US 8,449,113 B2
(45) Date of Patent: May 28, 2013

(54) IMAGING UNIT AND CONTROL METHOD THEREOF

(75) Inventor: Masao Shikaumi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 5 days.

(21) Appl. No.: 13/208,702

(22) Filed: Aug. 12, 2011

(65) Prior Publication Data

US 2012/0050673 A1    Mar. 1, 2012

(30) Foreign Application Priority Data

Aug. 31, 2010   (JP) .................................. 2010-195062

(51) Int. Cl.
*A61B 3/14*   (2006.01)
*A61B 3/00*   (2006.01)

(52) U.S. Cl.
USPC .......................................... 351/206; 351/246

(58) Field of Classification Search
USPC ................................................ 351/200–246
See application file for complete search history.

(56) References Cited

U.S. PATENT DOCUMENTS

| | | | | |
|---|---|---|---|---|
| 7,926,946 B2* | 4/2011 | Ono et al. | ...................... | 351/206 |
| 2009/0323022 A1* | 12/2009 | Uchida | ......................... | 351/206 |
| 2011/0170063 A1* | 7/2011 | Ooban et al. | .................. | 351/206 |

FOREIGN PATENT DOCUMENTS

JP    10-179523 A    7/1998

* cited by examiner

*Primary Examiner* — Mohammed Hasan (74) *Attorney, Agent, or Firm* — Fitzpatrick, Cella, Harper & Scinto (57) ABSTRACT

An imaging unit detachable from an optical unit of an ophthalmologic imaging apparatus having a light source, an illumination optical system that directs light from the light source to a subject's fundus, and an imaging optical system that directs reflected light from the subject's fundus to an image sensing surface of an imaging device includes an imaging device that images a fundus image formed on an image sensing surface with the reflected light, and a display unit configured to display an image. The imaging unit has a live view function to perform continuous display on the display unit, of fundus images imaged by the imaging device, and switches a display of an image on the display unit by the live view function between a normal display and a display in which the normal display is vertically and horizontally inverted, in accordance with information regarding the imaging optical system.

11 Claims, 10 Drawing Sheets

IMAGING UNIT AND CONTROL METHOD THEREOF

BACKGROUND OF THE INVENTION

1. Field of the Invention

The present invention relates to an imaging unit used in an ophthalmologic imaging apparatus.

2. Description of the Related Art

A fundus camera that performs positioning and focusing by illuminating a fundus with visible light or infrared light, and performs fundus imaging with a strobe light is used conventionally in applications such as fundus diagnosis, diabetes medical examination, etc. In an application of a physical examination especially, a non-mydriasis fundus camera that is capable of imaging without using a mydriatic agent is mainly used. A non-mydriasis fundus camera like this avoids miosis of a subject's eye through the use of infrared light for illumination.

A single-lens reflex type camera may be used for still-image imaging of a fundus camera. In recent years, single-lens reflex digital cameras that form electronic images using image sensing devices such as CMOS and CCD etc. have been used for fundus imaging more often. A single-lens reflex digital camera that has a live view function which provides continuous display of images onto a liquid crystal display on the back surface of an image sensing device has also been released to the market.

However, commercially available single-lens reflex digital cameras are provided with a characteristic to filter out infrared light for the purpose of removing the influence of infrared light on color reproduction. An infrared-cutting characteristic has been realized by installing an optical member that reflects or absorbs infrared light at the front of an image sensing device.

Therefore, for infrared monitor observation in a non-mydriasis fundus camera, the live view function of a single-lens reflex digital camera was not able to be used as it was.

In view of the above situations, the present applicant, by removing an infrared-cutting characteristic from a single-lens reflex digital camera, have proposed an imaging unit for a fundus camera that can be used for observation by utilizing the live view function at the time of non-mydriasis.

However, there are a plurality of models of fundus cameras to which such an imaging unit is attached, and due to the application difference etc., optical characteristics or light source characteristics may vary, and therefore it may be necessary to prepare an imaging unit that is compatible with different fundus cameras. For example, due to differences in the optical system configuration, depending on the model of the fundus camera, there was a case where an image is formed on an image sensing device of an imaging unit with the vertical and horizontal directions inverted.

In this case, when performing observation using live view, in some fundus camera models, a normal image is displayed on its back surface, and in other models, a vertically and horizontally inverted image is displayed. If a vertically and horizontally inverted image is displayed in live view, position adjustment (alignment) for imaging will be very difficult.

In Japanese Patent Laid-Open No. 10-179523 (hereinafter, Patent Document 1), disclosed is a technique related to a digital camera that displays a live view of vertically and horizontally inverted images when attached to a fundus camera, and returns a live view display to a normal display when removed from the fundus camera. However, in Patent Document 1, a technique that changes a display direction of a live view depending on a model of a fundus camera to which the digital camera is attached is not mentioned.

Although a xenon tube is mainly used as an imaging light source of a fundus camera, luminance increase of a white LED has progressed recently, and an example in which a white LED is adopted as an imaging light source has also been found. However, a xenon tube differed in spectral characteristic as a light source greatly from a white LED, and white balance correction and color correction corresponding to each of the light sources were required in an imaging unit side.

In the latest digital cameras, there are also ones in which aberration correction of an imaging lens, such as light falloff at edges, chromatic aberration of magnification, distortion etc. is possible. A fundus camera is influenced especially by light falloff at edges, because the camera takes an image of a fundus of human-eyes that is not flat but spherical, and an imaging light source is used for imaging, and light distribution unevenness of the imaging light source is always included in the taken image, and so on. Since an imaging field angle and an optical characteristic differed depending on a model of a fundus camera, in the case of correcting optical aberration such as light falloff at edges, there was the necessity of preparing an imaging unit that was made to have corrective parameters corresponding to a model of a fundus camera.

As stated above, depending on the model of the fundus camera, an imaging unit corresponding to the direction of a live view display, a wavelength characteristic of a light source, or an optical characteristic such as light falloff at edges was needed to be prepared in each case, and this had become a cost up factor during production or management. Likewise, to a user who uses a plurality of sets of fundus cameras such as in medical examination applications, there was the necessity of operating an imaging unit fixedly in association with a model of a fundus camera, and this had forced disadvantages on a user in respect of management.

SUMMARY OF THE INVENTION

The present invention is made in view of the above-mentioned problems, and according to an embodiment thereof, provided is an imaging unit for an ophthalmologic imaging apparatus that realizes cost reduction with respect to production and management, and at the same time, also improves convenience for the user.

According to one aspect of the present invention, there is provided a control method of an imaging unit detachable from an optical unit of an ophthalmologic imaging apparatus having a light source, an illumination optical system that directs light from the light source to a subject's fundus, and an imaging optical system that directs reflected light from the subject's fundus to an image sensing surface of an imaging device, the imaging unit comprising an imaging device that images a fundus image formed on an image sensing surface with the reflected light and a display unit configured to display an image, the method comprising: a live view step of performing continuous display, on the display unit, of fundus images imaged by the imaging device; and a control step of switching a display of an image on the display unit in the live view step between a normal display and a display in which the normal display is vertically and horizontally inverted, in accordance with information regarding the imaging optical system of the optical unit.

Furthermore, according to another aspect of the present invention, there is provided an imaging unit detachable from an optical unit of an ophthalmologic imaging apparatus having a light source, an illumination optical system that directs light from the light source to a subject's fundus, and an imaging optical system that directs reflected light from the subject's fundus to an image sensing surface of an imaging device, the imaging unit comprising: an imaging device that images a fundus image formed on an image sensing surface with the reflected light; a display unit configured to display an image; a live view unit configured to perform continuous display, on the display unit, of fundus images imaged by the imaging device; and a control unit configured to switch a display of an image on the display unit by the live view unit between a normal display and a display in which the normal display is vertically and horizontally inverted, in accordance with information regarding the imaging optical system of the optical unit.

Further features of the present invention will become apparent from the following description of exemplary embodiments with reference to the attached drawings.

DESCRIPTION OF THE EMBODIMENTS

[First Embodiment]

Figure 1:
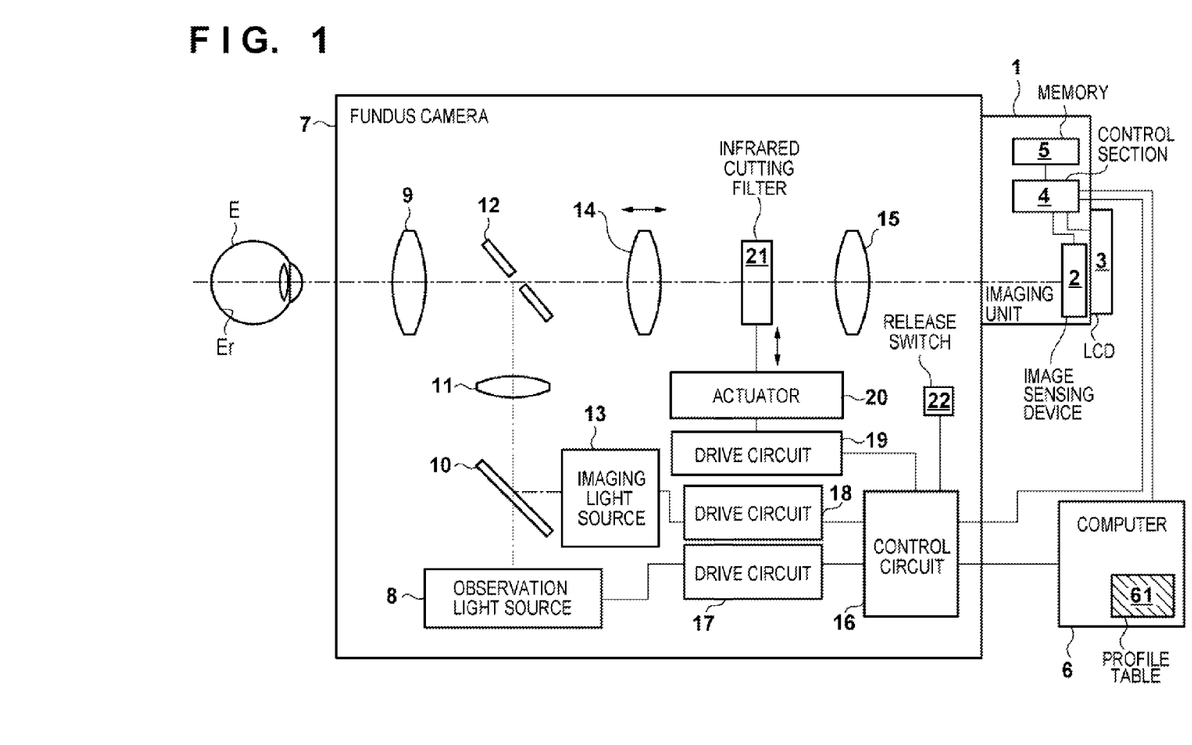
FIG. 1 is a block diagram of an ophthalmologic imaging apparatus according to a first embodiment.

FIG. 1 illustrates a block diagram of an imaging unit for an ophthalmologic imaging apparatus according to a first embodiment, and a fundus camera that is the ophthalmologic imaging apparatus to which it is attached. Reference numeral 1 denotes the imaging unit. The imaging unit 1 has a configuration of a single-lens reflex digital camera, and is attached to the fundus camera 7 in a way that can be detached. Accordingly, the imaging unit 1 can be attached to a plurality of models of fundus cameras. The ophthalmologic imaging apparatus according to the present embodiment is configured to include an optical unit (having an imaging light source, an observation light source, and an optical system) and an imaging unit that is detachable from the optical unit, and the optical unit is referred to as a fundus camera in the present specification.

An image sensing device 2, which is arranged inside the imaging unit 1, converts an optical image formed on an image sensing surface of the image sensing device 2 into an electrical signal. An output signal of this image sensing device 2 is connected to a control section 4 in the imaging unit 1, and after adding aberration correction, such as color correction and correction of light falloff at edges, etc. to this output signal, the control section 4 performs transformation processing into image data (so-called a development process.)

A liquid crystal display 3 that is a display section is provided on the back surface of the imaging unit 1, and an output of the control section 4 is connected thereto. The control section 4 carries out preview display of the image data imaged as a still image on the liquid crystal display 3. The control section 4 can perform a live view display by performing continuous display, on the liquid crystal display 3, of images formed on the image sensing device 2. Furthermore, by means of switching, etc. the sending sequence of the image data to the liquid crystal display 3 whether to send from the beginning or the end of the image data sequentially when performing a display on the liquid crystal display 3, it is possible to switch between a normal display of an image or a vertically and horizontally inverted image display. In addition, a memory 5 for storing various settings and programs, etc. is connected to the control section 4.

The imaging unit 1 requires near-infrared sensitivity in order to be used for non-mydriasis observation, and does not include an optical member that has an infrared-cutting characteristic and is arranged on the front surface of the image sensing device 2 in a usual single-lens reflex digital camera. Reference numeral 6 denotes a computer that is connected to the control section 4 of the imaging unit 1 and to a control circuit 16 of the fundus camera 7, via a USB and a serial port. The computer 6 has a table (hereinafter, a profile table 61) in which a model name of a fundus camera and information related to an imaging optical system is made to be in association with each other with respect to a plurality of kinds of fundus cameras. Examples of information related to the imaging optical system held in the profile table 61 includes the number of image formations in the optical system, a color correction parameter, an optical aberration correction parameter suitable for each fundus camera, etc.

The fundus camera 7 according to the present embodiment is a non-mydriasis fundus camera, and in the fundus camera 7, provided is the observation illumination optical system that extends from the observation light source 8 constituted by an infrared LED and irradiating an infrared light, to an object lens 9 that is arranged so as to correspond to a subject's eye E, for example. In this observation illumination optical system, the observation light source 8, a dichroic mirror 10, a relay lens 11 and a holey mirror 12 are sequentially arranged. In an incidence direction of the dichroic mirror 10, an imaging light source 13 constituted by a white LED or a xenon tube is arranged as an imaging illumination optical system. An observation illumination optical system and an imaging illumination optical system are named generically as an illumination optical system. That is, the illumination optical system directs the light from light sources of the observation light source 8 or the imaging light source 13 to a subject's fundus.

At the back of the holey mirror 12, as the imaging optical system, arranged is a focus lens 14 that moves in an optical axis direction and adjusts the focus. At the back of the focus lens 14, a relay lens 15 is arranged. The focus lens 14 and relay lens 15 make up a relay optical system that is an inversion imaging system. The relay optical system is for extending an optical path length in order to make a space for arranging, in fundus camera 7, each of elements that make up the imaging optical system in the fundus camera 7. Depending on a configuration of a fundus camera, a plurality of relay optical systems may be arranged, and a vertical direction of an image formed on the image sensing device 2 may change depending on whether odd numbers or even numbers of such relay optical systems are arranged. Details will be described later. On an extension of the optical-axis of this relay lens 15, the imaging unit 1 is attached detachably. That is, the observation optical system directs a reflected light from a fundus Er to the image sensing surface of the image sensing device 2. As mentioned above, the fundus camera 7 as an optical unit has a light source, an illumination optical system and an imaging optical system.

In the fundus camera 7, the control circuit 16 is provided, and outputs of the control circuit 16 are connected to the observation light source 8 and the imaging light source 13 via a drive circuit 17 and a drive circuit 18, respectively. In addition, the control circuit 16 is also connected to the control section 4 in the imaging unit 1, and a release switch 22 provided in the fundus camera 7.

In addition, the control circuit 16 is connected to an actuator 20 via a drive circuit 19. The actuator 20, when driven, inserts/retracts an infrared cutting filter 21 in/from an imaging optical path. This infrared cutting filter 21 has the same characteristics as the infrared-cutting characteristics removed from the imaging unit 1. At the time of observation, by retracting the infrared cutting filter 21 outside the imaging optical path, the fundus image observation by the imaging unit 1 becomes possible. At the time of imaging, by inserting the infrared cutting filter 21 in the imaging optical path, spectral characteristics equivalent to the usual single-lens reflex digital camera are acquired by the imaging unit 1 and the infrared cutting filter 21, and imaging becomes possible. The control circuit 16 can be constituted by a one-chip microcomputer etc., and in a not-shown built-in or external nonvolatile memory, various adjustment values are recorded. When the release switch 22 is pushed, the control circuit 16 transmits a release signal to the control section 4 of the imaging unit 1, and thereby, an imaging operation is performed by the imaging unit 1.

In the fundus camera 7, the light source and the optical system have a difference depending on a model. Hereinafter, an influence of the difference depending on a model will be described. First, using FIGS. 2A to 2D, relation between the number of relay optical systems arranged that is an inversion imaging system and the direction of an image that is formed will be described. FIGS. 2A to 2D are diagrams illustrating the optical system of the fundus camera 7 according to the first embodiment.

The single-lens reflex digital camera that is a base of the imaging unit 1 is, originally, an imaging system in which inversion is effected once, and in the case of carrying out imaging with a usual imaging lens attached thereto, an inverted image is formed on the image sensing device 2. At this time, a normal image is displayed on the liquid crystal display 3. That is, in the display of a normal state (normal display) in the live view, an image formed on the image sensing surface of the image sensing device 2 is displayed in an inverted state.

Figure 2A:
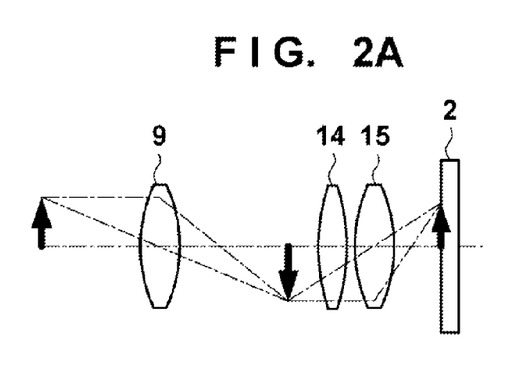
FIGS. 2A to 2D are diagrams illustrating an optical system of a fundus camera according to the first embodiment.
Figure 2B:
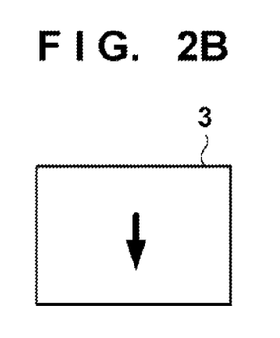

In the model of the fundus camera 7 including an image forming system in which, including a relay optical system, image formation is effected in an even number of times (hereinafter, this type of image forming system is referred to as "even-number image forming system"), an image formed on the image sensing device 2 is a normal image. FIG. 2A illustrates an example of a model in which one relay optical system, that is a set of the focus lens 14 and the relay lens 15, is inserted, resulting in an image forming system in which image formation is effected twice. In this case, a normal image is formed on the image sensing device 2, as illustrated in FIG. 2A. Therefore, if the control section 4 of the imaging unit 1 does not invert the displayed image, an inverted image is displayed on the liquid crystal display 3 as illustrated in FIG. 2B.

If the displayed image remains inverted, the manipulating direction and the change direction of the display is opposite to a usual state in the alignment to the fundus, and therefore it is very difficult to carry out manipulation. Therefore, when the imaging unit 1 is attached to the fundus camera 7 of such a model and is used, it is necessary for the control section 4 to invert the image in normal display on the liquid crystal display 3 vertically and horizontally so as to be displayed in the right direction.

Figure 2C:
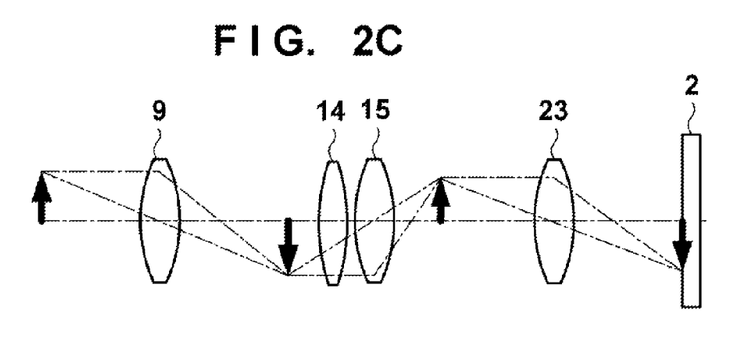
Figure 2D:
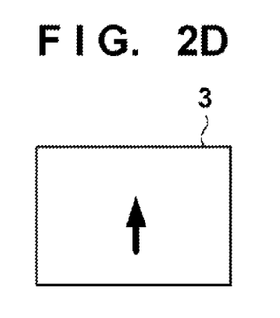

On the other hand, in the model of the fundus camera 7 including an image forming system in which, including a relay optical system, image formation is effected in an odd number of times (hereinafter, this type of image forming system is referred to as "odd-number image forming system"), an image formed on the image sensing device 2 is an inverted image. FIG. 2C illustrates an example of a model in which at the back of a relay optical system (a set of the focus lens 14 and the relay lens 15) a relay optical system 23 is inserted, resulting in an image forming system in which image formation is effected three times. In this case, an inverted image is formed on the image sensing device 2, as illustrated in FIG. 2C. Therefore, a normal image is displayed on the liquid crystal display 3, as illustrated in FIG. 2D.

Figure 3A:
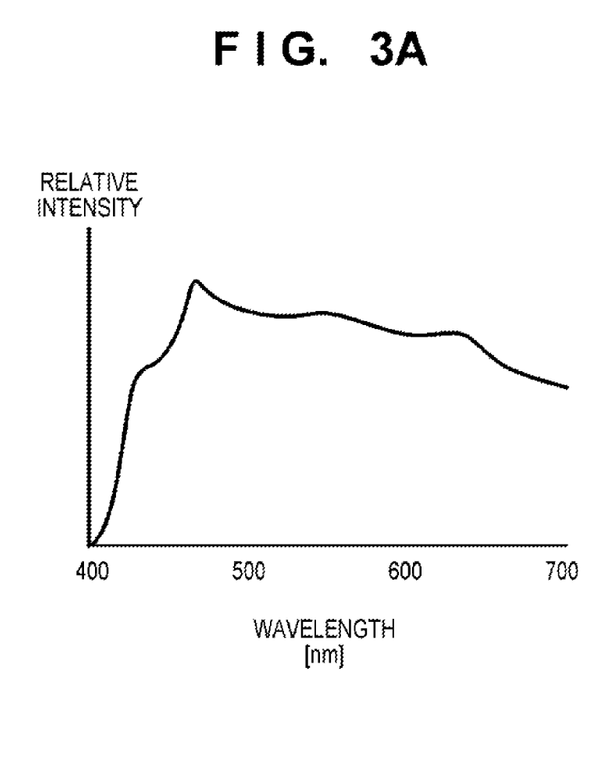
FIGS. 3A and 3B are graphs illustrating a spectral characteristic of an imaging light source.
Figure 3B:
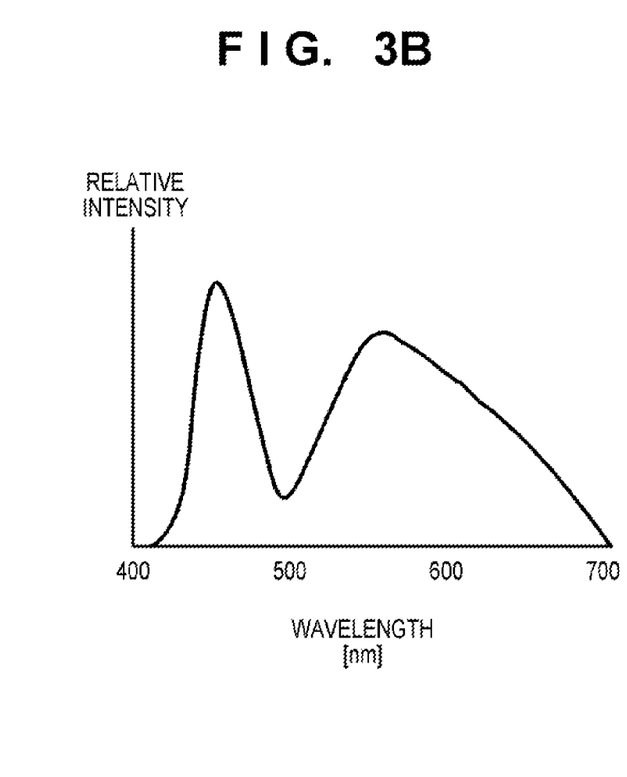

Next, a difference in an imaging light source is described using FIGS. 3A and 3B. FIGS. 3A and 3B are graphs illustrating spectral characteristics of an imaging light source. As the imaging light source 13 of the fundus camera 7, a xenon tube has been used generally. In these days, a model in which a white LED is used as the imaging light source 13 also exists. An example of a spectral characteristic of a visible spectrum of a xenon tube is illustrated in FIG. 3A. An example of a spectral characteristic of a visible spectrum of a white LED is illustrated in FIG. 3B. As a white LED, in a type in which a white light is realized with a blue LED and a fluorescent material, the spectral characteristic has a peak in the light-emitting wavelength of the blue LED as illustrated in FIG. 3B, and is different greatly from the spectral characteristic of the xenon tube. Therefore, parameters of color correction for an image obtained by imaging will differ greatly depending on the kind of light source used as an imaging light source.

Figure 4:
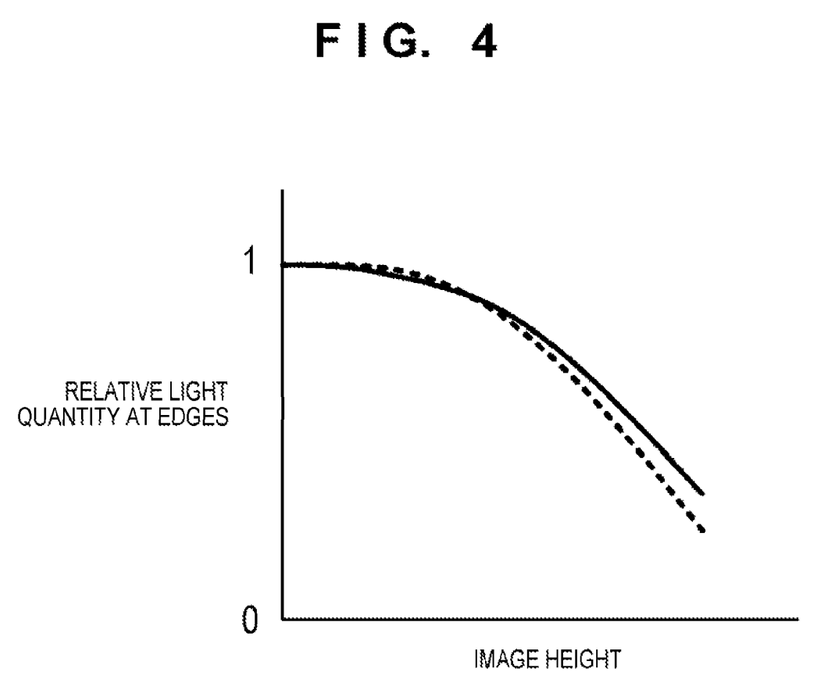
FIG. 4 is a graph illustrating difference in light-quantity at edges characteristics depending on the model of the fundus camera.

Next, a difference in a light falloff at edges characteristic depending on a difference of an optical system is described using FIG. 4. FIG. 4 is a graph illustrating a difference in a light quantity at edges characteristic depending on the model of the fundus camera. Since an imaging light source is always used in a fundus camera at the time of imaging, the graph illustrates characteristics including not only characteristics of an imaging optical system but light distribution characteristics of an imaging light source.

In FIG. 4, it is illustrated how light quantity changes depending on an image height with an optical axis center set to 0, and relative light quantity in the case of the light quantity of the center being set to 1 is plotted. Each of a solid line and a dotted line illustrates an example of a characteristic when a model is different. Since a configuration of a light source or an optical system is different depending on a model of a fundus camera, a characteristic of light falloff at edges is different. In the case of performing correction of the light falloff at edges, there is the necessity of changing a correction characteristic depending on the model. A description with respect to light quantity at edges has been carried out here, and since, with respect to other optical aberrations such as chromatic aberration of magnification and distortion, a characteristic is different depending on a model of a fundus camera, there is the necessity of changing the correction characteristic for every model in the case of performing correction similarly.

Figure 5:
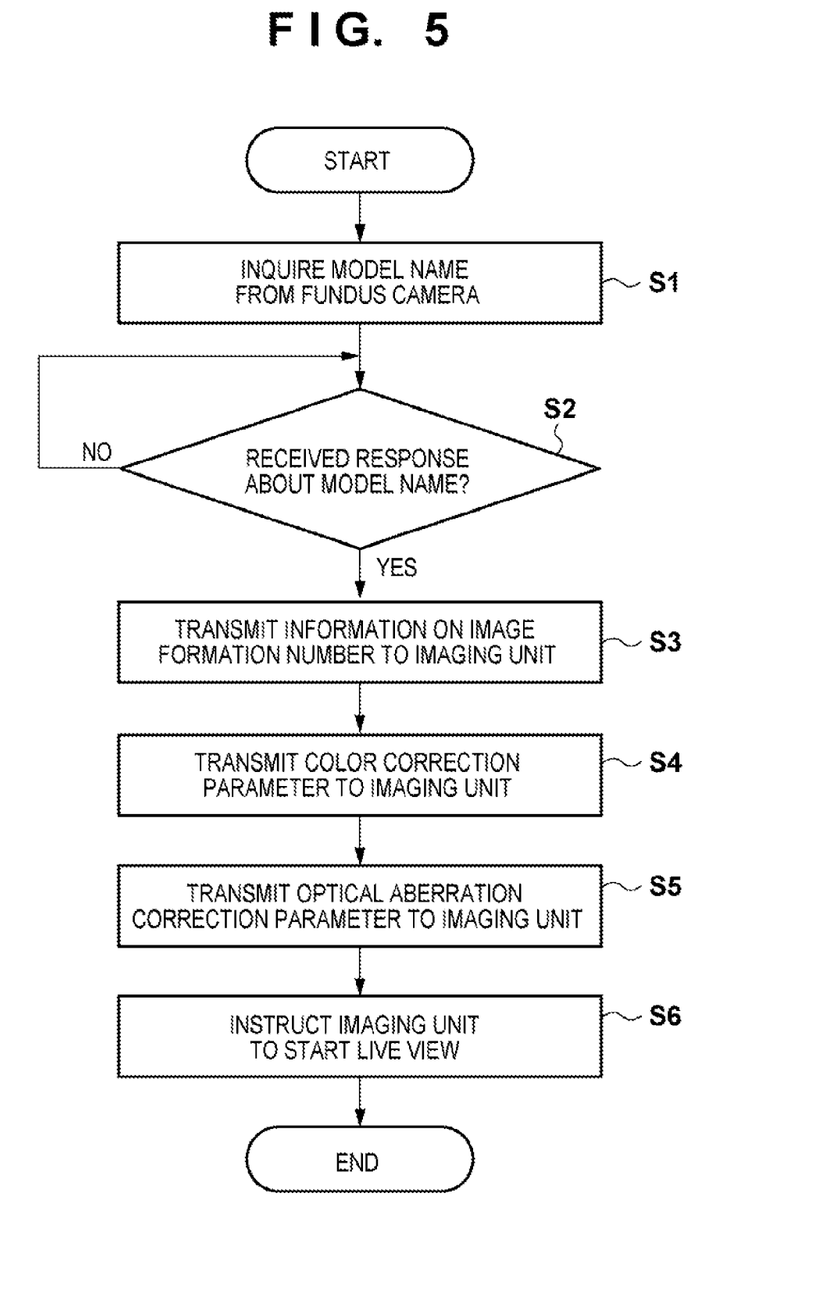
FIG. 5 is a flow chart illustrating an operation of a computer according to the first embodiment.

Next, an operation according to the present embodiment will be described using flow charts of FIG. 5 to FIG. 7. FIG. 5 illustrates a flow chart of an operation of the computer 6. This process may be realized by the computer 6 executing a program stored in a not-shown memory. When the computer 6 is powered on, first in Step S1, the computer 6 acquires the model name of the fundus camera 7 to which the imaging unit 1 is attached. In the present embodiment, the computer 6 inquires the model name of the fundus camera 7 of the control circuit 16 of the fundus camera 7 via a USB or a serial port. This communication may be carried out through a cable or a wireless system. This is because, depending on a model of the fundus camera 7, there exist a difference in the number of image formations in an imaging optical system, a difference in a color correction characteristic due to a difference of an imaging light source, and differences in an optical aberration characteristic and a light distribution characteristic at the time of imaging. Information about every fundus camera 7 model that is connectable is stored in the profile table 61 within computer 6 in advance.

In Step S2, the computer 6 waits for a response of the model name, and when acquiring the response, makes the process go to Step S3, and then, transmits, to the imaging unit 1, the image-forming number information of the imaging optical system corresponding to the model name acquired in Step S2. Next, in Step S4, the computer 6, similarly as in Step S3, transmits the color correction parameter corresponding to the fundus camera model name to the imaging unit 1. As a color correction parameter, color temperature information that determines a white balance, a color shift quantity of a blue-umber axis and a green-magenta axis, look-up table (LUT) data with respect to each color of R, G, and B, etc. are enumerated, for example.

Next, in Step S5, the computer 6 transmits the optical aberration correction parameter corresponding to the fundus camera model name to the imaging unit 1. As an optical aberration correction parameter, in the case of the light falloff at edges correction, for example, the characteristics, as described in FIG. 4, of the relative light quantity at edges corresponding to the image height are transmitted. In the above-mentioned example, the parameters of the light falloff at edges correction as the optical aberration correction parameter have been described, and other than that, the correction parameter of magnification aberration and distortion can also be used as an optical aberration correction parameter, for example. Next, in Step S6, the computer 6 transmits, the command to make the imaging unit 1 start a live view. The communication between the computer 6 and the imaging unit 1 may be carried out through a cable or a wireless system. As another alternative, a configuration so that the imaging unit 1 has the function of the computer 6 built in may be possible.

Figure 6:
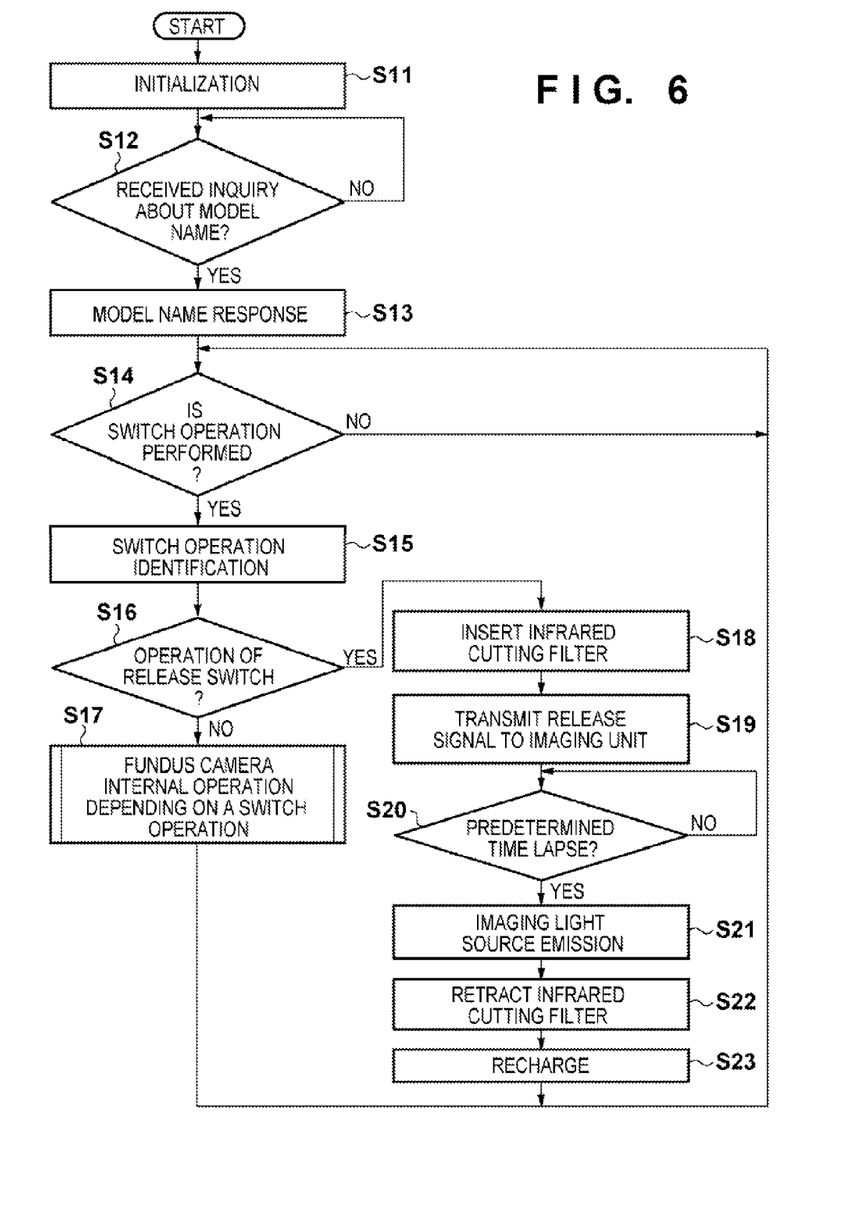
FIG. 6 is a flow chart illustrating an operation of the fundus camera according to the first embodiment.

FIG. 6 is a flow chart illustrating an operation of the fundus camera 7. This operation is realized by a not-shown CPU in the control circuit 16 executing a program stored in a not-shown memory. First, when the power is turned on and the operation starts, the control circuit 16 will performs initialization, etc. of an internal state of the fundus camera 7, etc. in Step S11. Next, in Step S12, the control circuit 16 waits for an inquiry about a model name from the computer 6 described in Step S2 of FIG. 5. When receiving a model name inquiry, the control circuit 16 makes the process go to Step S13 and sends back the model name.

Next, in Step S14, the control circuit 16 waits for a switch operation to be carried out, and repeats this Step S14 until the switch operation is performed, and when the switch operation is performed, makes the process go to Step S15, and then identifies the operated switch. Subsequently, in Step S16, the control circuit 16 judges whether the operated switch is the release switch 22. If it is judged that the operated switch is not the release switch 22, the control circuit 16 makes the process go to Step S17, and performs internal processing of the fundus camera 7 corresponding to the switch operation. Then, the process returns to Step S14.

In Step S16, when it is judged that the release switch 22 has been operated, the control circuit 16 makes the process go to Step S18, and then inserts the infrared cutting filter 21 into the imaging optical path via the drive circuit 19 and the actuator 20. Then, the control circuit 16 makes the process go to Step S19, and transmits the release signal to the control section 4 of the imaging unit 1. Next, in Step S20, the control circuit 16 waits for a lapse of a predetermined time in order to match the shutter open timing of the imaging operation of the imaging unit 1 with the light-emitting timing of the imaging light source 13. Then, when the predetermined time elapses, the control circuit 16 makes the process go to Step S21, and makes the imaging light source 13 emit light to carry out imaging. Then, in Step S22, the control circuit 16 retracts the infrared cutting filter 21 from the imaging optical path via the actuator 20 and the drive circuit 19 again. Then, in Step S23, the control circuit 16 recharges a stroboscope of the imaging light source 13, and makes the process returns to Step S14. However, in the case of the imaging light source 13 being a white LED, the recharging step of Step S23 is not necessarily required.

Figure 7:
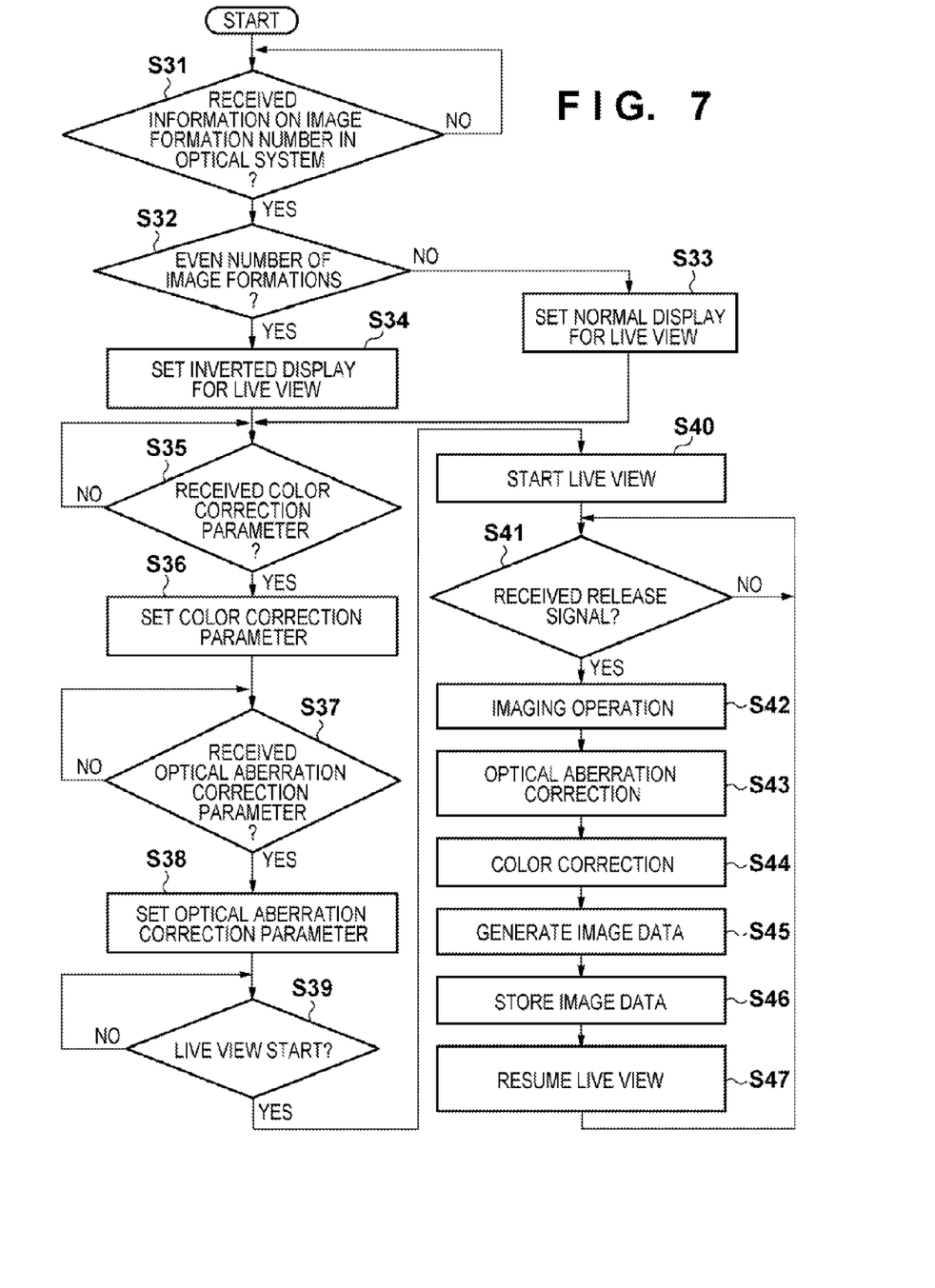
FIG. 7 is a flow chart illustrating an operation of an imaging unit according to the first embodiment.

FIG. 7 is a flow chart illustrating an operation of the imaging unit 1. This process is realized by the control section 4 in the imaging unit 1 executing a program stored in the memory 5. With the power turned on, in Step S31 first, the control section 4 waits for the optical system image-forming number information to be transmitted from the computer 6 as described in Step S3 of FIG. 5. When the optical system image-forming number information is received, the process will go to Step S32.

In Step S32, the control section 4 determines whether the received optical system image-forming number is an even number or an odd number. In the case of an odd number, the control section 4 performs setting therein so that the display will be a normal rotation display (normal display) at the time of the live view (Step S33). Then, the process goes to Step S35. On the other hand, when, in Step S32, the optical system image-forming number is judged to be an even number, the control section 4 performs setting therein so that a display will be a vertically and horizontally inverted display (display in which the normal display is vertically and horizontally inverted) at the time of the live view (Step S34). Then, the process goes to Step S35. In this way, depending on whether the imaging optical system of the fundus camera 7 is an odd-number image forming system or an even-number image forming system, an image displayed on the liquid crystal display 3 is switched, in live view, between a normal display or a display in which the image is vertically and horizontally inverted.

In Step S35, the control section 4 waits for receiving, from the computer 6, the color correction parameter corresponding to the model of the imaging unit 1. Then, when receiving the color correction parameter, the control section 4 sets this color correction parameter in the memory 5 in Step S36. Next, the control section 4 waits for receiving, from the computer 6, the optical aberration correction parameter corresponding to the model of the imaging unit 1 in Step S37. Then, when receiving the optical aberration correction parameter, the control section 4 sets this optical aberration correction parameter in the memory 5 in Step S38.

Next, the process goes to Step S39, and the control section 4 waits for receiving a command to start a live view from the computer 6 in Step S6 of FIG. 5. When the control section 4 receives a command to start a live view, the control section 4 starts a live view operation in Step S40, and uses the imaging unit 1 as an observation device. That is, the control section 4 makes the observation light source 8 emit light, retracts the quick return mirror in the imaging unit 1, opens the shutter (not-shown), reads out sequentially fundus images formed on the image sensing device 2, and performs a display on the liquid crystal display 3. At this time, depending on the contents that were set in Step S33 or Step S34 corresponding to the model of the fundus camera 7 to which the imaging unit is attached, the display direction of the live view is normal or vertically or horizontally inverted. The above operation is continued during the live view displaying.

Next, the process goes to Step S41, and the control section 4 checks whether a release signal has been received from the fundus camera 7 as a result of Step S19 of FIG. 6. In Step S41, when the release signal is not able to be received, Step S41 is repeated. When a release signal is received, the process goes to Step S42.

In Step S42, the control section 4 starts the imaging operation of a still image, and performs accumulation of the still images on the image sensing device 2 during a predetermined period. In the process of performing the accumulation, the imaging light source 13 emits light in Step S21 of FIG. 6, and imaging is performed. Then, read-out of the still images is performed. Next, the process goes to Step S43, where the control section 4 performs optical aberration correction using the optical aberration correction parameter stored in the memory 5 in Step S38. Next, the process goes to Step S44, and the control section 4 performs color correction for the still images read out using the color correction parameter stored in the memory 5 in Step S36.

The control section 4 performs development processing for making image files in formats such as JPEG with respect to the image data with the optical aberration correction and the color correction performed thereon as mentioned above (Step S45), and records the images on a not-shown storage medium in the imaging unit 1 (Step S46). As another alternative, the still images (image files) may be sent to the connected computer 6. When the still-image-imaging is completed, the process goes to Step S47, and the control section 4 resumes the live view, and after that, returns the process to Step S41.

Although, in an above description of first embodiment, an example in which image-forming number information of an optical system is transmitted has been described, only information on the number of image formations being an even number or an odd number may be sent. Only other information corresponding uniquely to information on the number of image formations being an even number or an odd number, for example, information on the direction of the live view display being normal or inverted may be sent. The computer 6 may be built in the imaging unit 1.

As mentioned above, according to the first embodiment, it is possible to use the same imaging unit regardless of the model of a fundus camera, and achieve cost reduction with respect to production and management. It is possible to improve convenience also for the user. Since the model name and various parameters (the number of image formations, a parameter of a light falloff at edges correction, a color correction parameter, an optical aberration correction parameter, etc.) are held in association with each other in the profile table 61, it is possible to deal with an addition of a model, etc. flexibly, which is convenient.

[Second Embodiment]

Figure 8:
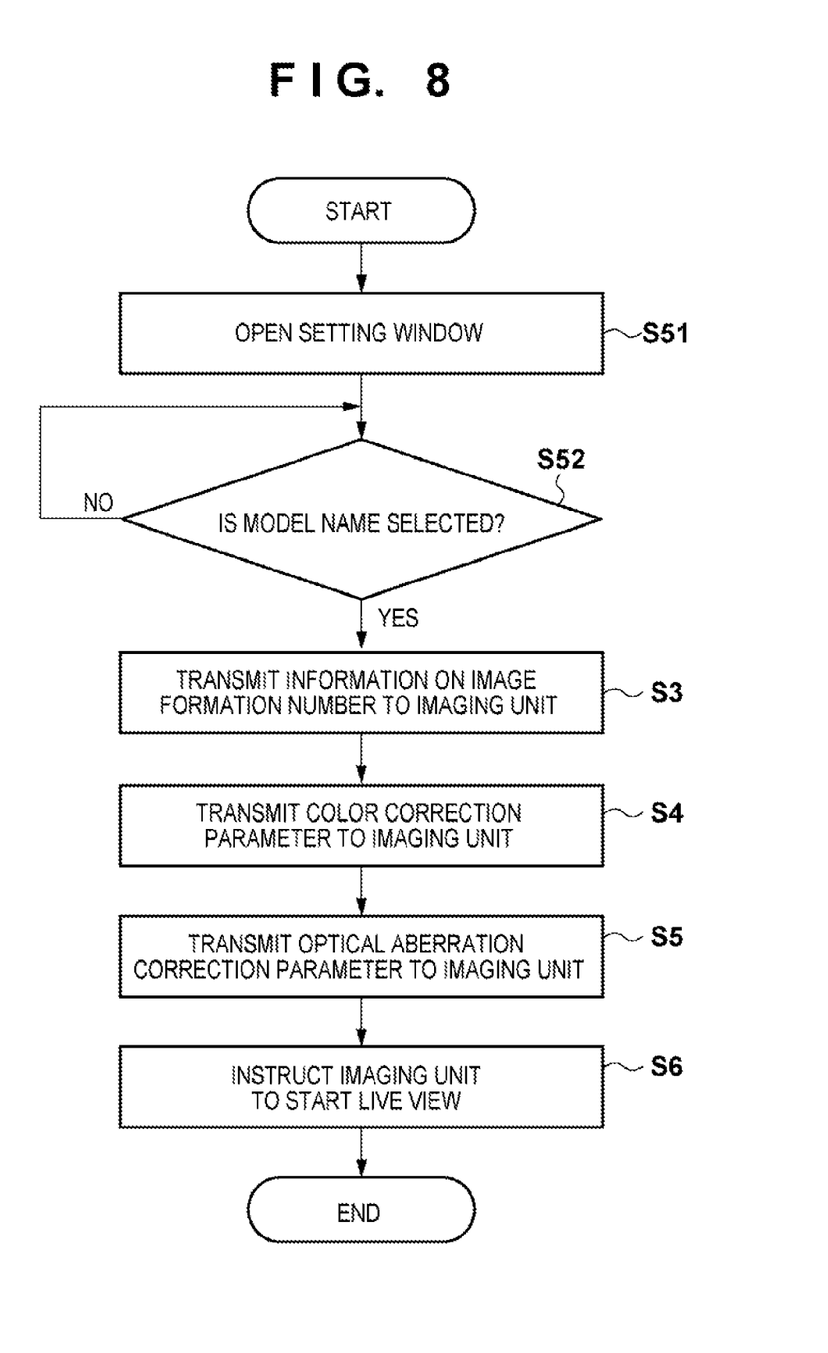
FIG. 8 is a flow chart illustrating an operation of a computer according to a second embodiment.

A first embodiment was an embodiment in which the computer 6 acquired model information of the fundus camera 7 automatically, and performed required parameter setting to the imaging unit 1. However, the model information may be set up manually by making a user select a model name on a setting window of the computer 6. A second embodiment is such an embodiment. Hereinafter, an operation of a second embodiment will be described using flow charts of FIG. 8 to FIG. 9. FIG. 8 corresponds to FIG. 5 of the first embodiment, FIG. 9 corresponds to FIG. 6 of the first embodiment, the same number is given to the step of the same operation, and detailed description is omitted.

FIG. 8 is a flow chart illustrating an operation by the computer 6 according to the second embodiment. In the flow chart illustrated in FIG. 5, the steps of S1 and S2 that inquire the model name of a fundus camera are deleted, and Step S51 that opens a setting window and Step S52 that waits for a user to select a model name of the fundus camera 7 are added instead. In the second embodiment, via setting window (user interface) like this, the model name of the fundus camera 7 is acquired by receiving an input from a user with respect to the model name of the fundus camera 7 to which the imaging unit 1 is attached.

In Step S51, the computer 6 opens a setting window on the screen, and displays side by side model names (model names registered in the profile table 61) of selectable fundus cameras, and makes the user select the model of fundus camera connected currently. If the user selects a model name, the process goes to Step S3, and Step S52 will be repeated until the user selects a model name. Since, Step S3 and subsequent steps are the same as those of the first embodiment, descriptions thereof are omitted.

Figure 9:
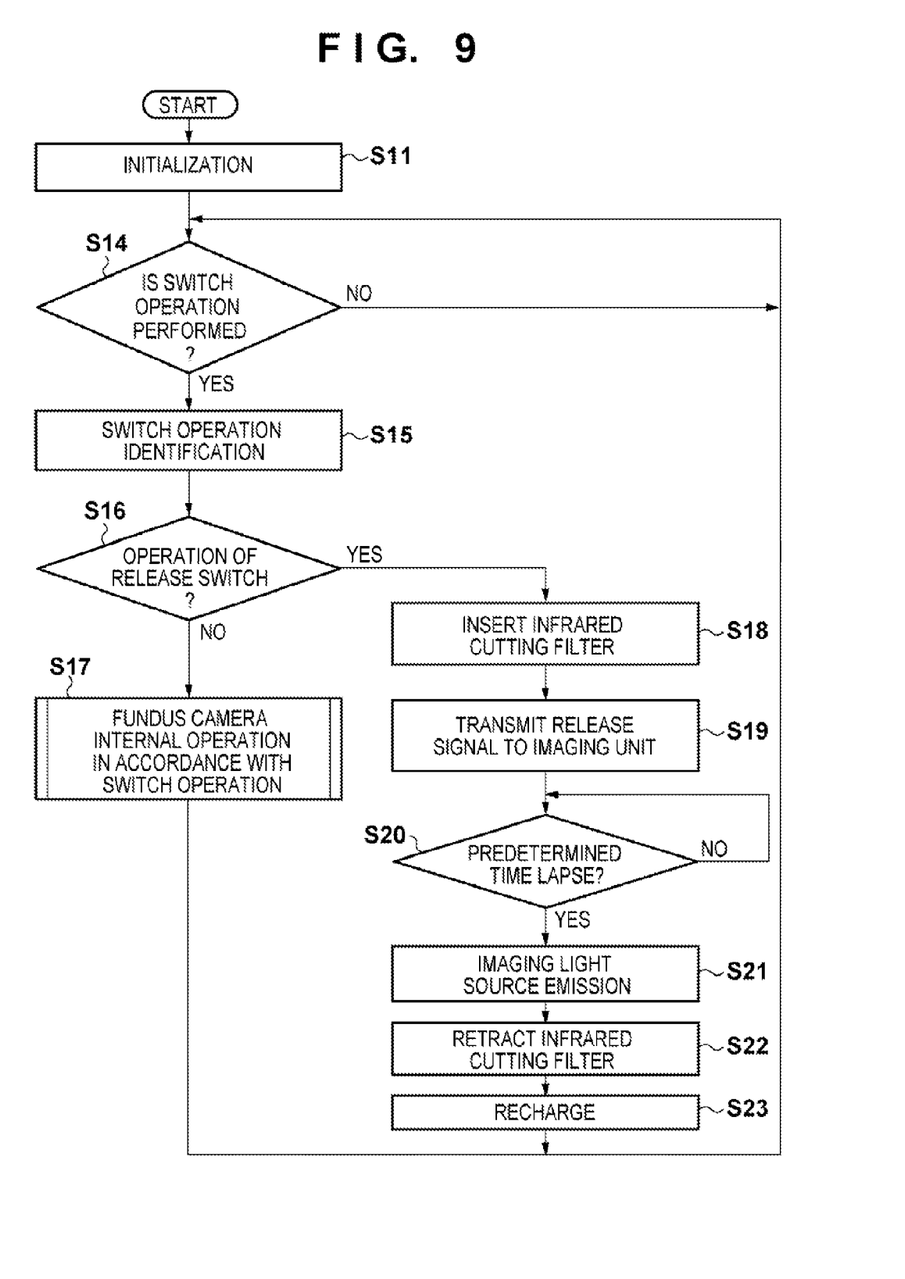
FIG. 9 is a flow chart illustrating an operation of a fundus camera according to the second embodiment.

FIG. 9 illustrates a flow chart of an operation of the fundus camera 7 according to the second embodiment. In the flow chart described in FIG. 6, Step S12 and S13 in which a model name is sent back to the computer 6 are deleted. The other steps are the same as those of the first embodiment.

With configuring as mentioned above, according to the second embodiment, even if the fundus camera 7 side is an old model that does not support an inquiry about the model name from the computer 6, there is an effect that the present invention can be applied.

[Third Embodiment]

Whether an imaging optical system is an even-number image forming system or an odd-number image forming system can also be judged automatically from the information of which of the subject's eye, right or left, is currently being imaged, and from a papilla position of an imaged fundus image. A third embodiment is such an embodiment. In addition, in the fundus camera, which eye, right or left, is to be imaged can be identified by a heretofore known art from the relative position relation between a subject's face position and a camera head section such as an imaging optical system.

Figure 10A:
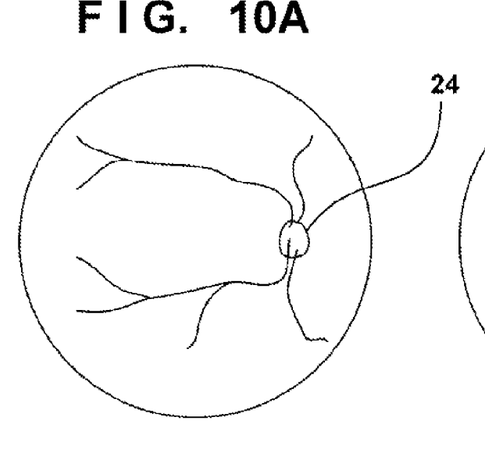
FIGS. 10A and 10B are figures illustrating a fundus image acquired by an ophthalmologic imaging apparatus.
Figure 10B:
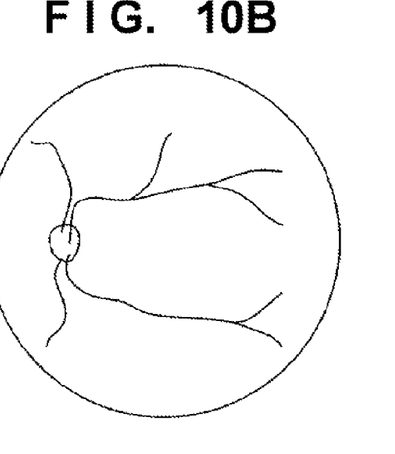

FIGS. 10A and 10B illustrate schematically a fundus image imaged using the fundus camera 7 according to a third embodiment. Reference numeral 24 denotes an optic nerve papilla part that is reflected most brightly in a fundus image. Therefore, position detection can be carried out easily by a known image processing technique. FIG. 10A illustrates a normal image of a right eye, and when imaged by an odd-number image forming system, such an image will be acquired. FIG. 10B illustrates a vertically and horizontally inverted image, and when imaged by an even-number image forming system, such an image will be acquired. That is, in the case of an imaged image of a right eye, if a papilla is on the right hand side, it is a normal image, and if a papilla is on the left hand side, it can be determined that it is an inverted image. In the case of an imaged image of a left eye, the relation with a papilla position becomes reverse. Since detection of a papilla position is easy as mentioned above, depending on the information on the right or left eye, it is possible to determine whether the fundus camera 7 attached to an ophthalmologic imaging apparatus is an even-number image forming system or an odd-number image forming system. In addition, it is easiest to use the position of an optic nerve papilla part among the anatomical parts in a fundus image, and this is used in the present embodiment, and however, the present invention is not limited to this. For example, it may be made to determine whether an even-number image forming system or an odd-number image forming system using a blood vessel running pattern as illustrated in FIGS. 10A and 10B, and a macula-lutea position.

Figure 11:
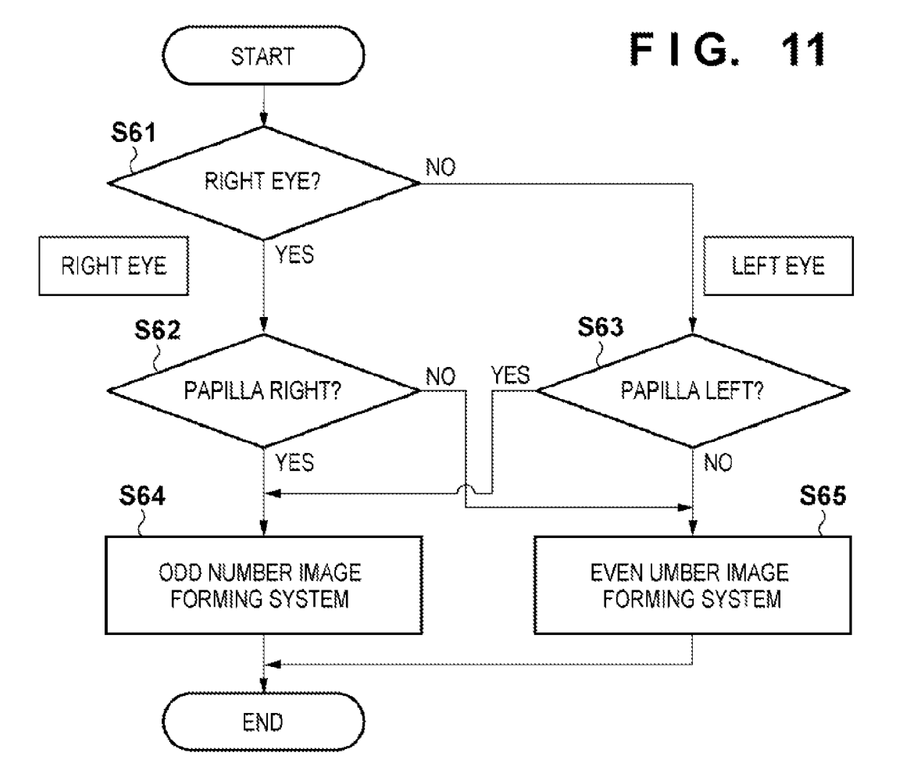
FIG. 11 is a flow chart illustrating an operation of a computer according to a third embodiment.

FIG. 11 is a flow chart illustrating a process in which the computer 6 according to the third embodiment judges whether the imaging optical system of the fundus camera 7 is an even-number image forming system or an odd-number image forming system. When the judgment started, the computer 6 identifies first whether the imaged image is a subject's right eye or a left eye (Step S61). In the case of the identified result being a right eye, the process goes to Step S62, and in the case of a left eye, the process goes to Step S63.

In Step S62, the computer 6 judges whether in the imaged fundus image, a papilla position is on the right hand side or not. Since in the fundus image of a right eye, the image is a normal image in the case of a papilla position being on the right hand side, the process goes to Step S64, and the computer 6 judges that the observation imaging system of the fundus camera 7 is an odd-number image forming system. Since the image is vertically and horizontally inverted image when a papilla is judged to exist on the left hand side at Step S62, the process goes to Step S65, and the computer 6 judges that the observation imaging system of the fundus camera 7 is an even-number image forming system.

On the other hand, in the case of the fundus image of a left eye, in Step S63, the computer 6 judges whether the papilla position of the imaged fundus image is on the left hand side or not. Since in the fundus image of a left eye, the image is a normal image in the case of a papilla position being on the left hand side, the process goes to Step S64, and the computer 6 judges that the observation imaging system of the fundus camera 7 is an odd-number image forming system. Since in the fundus image of a left eye, in the case of a papilla position being on the right hand side, the image is a vertically and horizontally inverted image, the process goes to Step S65, and the computer 6 judges that the observation imaging system of the fundus camera 7 is an even-number image forming system. Since the other operations are the same as those of the first embodiment, descriptions thereof are omitted.

As mentioned above, according to the third embodiment, there is an effect that whether the optical system of the fundus camera 7 is an even-number image forming system or an odd-number image forming system is determined automatically by imaging only one image of a human eye.

As described above, according to the embodiments described above, it is not necessary to prepare a separate imaging unit for every model of a fundus camera, and cost of management or production can be reduced. Also for a user who manages many fundus cameras like a medical examination vendor, there is an effect enhancing convenience of the user, because it is not necessary to fix combinations for every model of an imaging unit and a fundus camera.

In addition, the present invention is not limited to contents described in the embodiments, and various modifications etc. are possible. For example, although a xenon tube and a white LED were described as an imaging light source, the present invention is applicable also to a model that uses other light sources such as a LED of three colors of R, G, and B, and a laser light source, for example.

Also a configuration is possible in which the number of image formations of an observation optical system and every correction parameter itself may be acquired from the fundus camera 7, rather than a model name being acquired from the fundus camera 7. The imaging unit 1 according to the embodiments described above is capable of:

Switching of a live view between a normal display and a vertically or horizontally inverted display;

Setting of correction contents by an optical aberration correction parameter; and Setting of correction contents by a color correction parameter, and the like. However, an imaging unit capable of performing one of these or an arbitrary combination thereof is also within the scope of the present invention.

In the above described embodiments, the infrared-cutting filter 21 is inserted in an optical path at the time of imaging has been described, but since almost no infrared component is included in the case of a white LED imaging light source, a configuration is possible in which the infrared cutting filter 21 is not used and only color correction is addressed.

According to an imaging unit of the present invention, there is an effect that it is possible to use a same imaging unit regardless of the model of a fundus camera, and achieve cost reduction.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-195062, filed Aug. 31, 2010, which is hereby incorporated by reference herein in its entirety.

What is claimed is:

1. An imaging unit detachable from an optical unit of an ophthalmologic imaging apparatus, the optical unit comprising (a) a light source, (b) an illumination optical system that directs light from the light source to a subject's fundus, and (c) an imaging optical system that directs reflected light from the subject's fundus to an image sensing surface of an imaging device, the imaging unit comprising:

an imaging device that images a fundus image formed on an image sensing surface with the reflected light;

a display unit configured to display fundus images image by the imaging device; and a control unit configured to switch a display of an image on the display unit between a normal display and a display in which the normal display is vertically and horizontally inverted, in accordance with information regarding the imaging optical system of the optical unit.

2. The imaging unit according to claim 1, further comprising:
a holding unit configured to hold a table regarding a plurality of kinds of optical units in which their model names are associated with information indicating whether the number of image formations in their imaging optical systems is an odd number or an even number; and
an acquisition unit configured to acquire the model name of the optical unit to which the imaging unit is attached,
wherein the control unit, by acquiring information associated with the model name acquired by the acquisition unit from the table, determines whether the number of image formations in the imaging optical system of the optical unit is an odd number or an even number, and in accordance with the determination, switches a display of an image on the display unit between a normal display or a display in which the normal display is vertically and horizontally inverted.

3. The imaging unit according to claim 2, wherein the acquisition unit inquires of the optical unit to which the imaging unit is attached, about its model name, and acquires the model name from the optical unit.

4. The imaging unit according to claim 2, wherein the acquisition unit receives an input, by a user, of the model name of the optical unit to which the imaging unit is attached.

5. The imaging unit according to claim 2, wherein the table further includes color correction parameters suitable for optical units in association with model names, and
wherein the imaging unit further comprises a color correction unit configured to perform color correction of an image imaged by using the imaging device, using a color correction parameter associated with a model name acquired by the acquisition unit.

6. The imaging unit according to claim 2, wherein the table further includes optical aberration correction parameters suitable for optical units in association with model names, and
wherein the imaging unit further comprises an aberration correction unit configured to perform optical aberration correction of an image imaged by the imaging device using an optical aberration correction parameter associated with a model name acquired by the acquisition unit.

7. The imaging unit according to claim 6, wherein an aberration corrected by the aberration correction unit includes any of light falloff at edges correction, chromatic aberration of magnification, and distortion.

8. The imaging unit according to claim 1, further comprising:
a determination unit configured to determine whether a subject's eye imaged by the imaging unit is a left eye or a right eye; and
a detection unit configured to detect a papilla position from a fundus image of the imaged subject's eye,
wherein the control unit, based on the determination result of the determination unit and the papilla position detected by the detection unit, determines whether the number of image formations in an imaging optical system to which the imaging unit is attached is an odd number or an even number, and switches a display of an image on the display unit between a normal display or a display in which the normal display is vertically and horizontally inverted.

9. The imaging unit according to claim 1, wherein the display unit performs continuous live view display of fundus images imaged by the imaging device.

10. A control method of an imaging unit detachable from an optical unit of an ophthalmologic imaging apparatus, the optical unit comprising (a) a light source, (b) an illumination optical system that directs light from the light source to a subject's fundus, and (c) an imaging optical system that directs reflected light from the subject's fundus to an image sensing surface of an imaging device, the imaging unit comprising an imaging device that images a fundus image formed on an image sensing surface with the reflected light, the method comprising:
a display step of displaying, on a display unit, fundus images imaged by the imaging device; and
a control step of switching a display of an image on the display unit in the display step between a normal display and a display in which the normal display is vertically and horizontally inverted, in accordance with information regarding the imaging optical system of the optical unit.

11. An ophthalmologic imaging apparatus comprising:
an optical unit comprising (a) a light source, (b) an illumination optical system that directs light from the light source to a subject's fundus, and (c) an imaging optical system that directs reflected light from the subject's fundus to an image sensing surface of an imaging device; and
an imaging unit detachable from the optical unit, wherein the imaging unit comprises (a) an imaging device that images a fundus image formed on an image sensing surface with the reflected light, (b) a display unit configured to display fundus images imaged by the imaging device, and (c) a control unit configured to switch a display of an image on the display unit between a normal display and a display in which the normal display is vertically and horizontally inverted, in accordance with information regarding the imaging optical system of the optical unit.

* * * * *